(12) United States Patent
Huq

(10) Patent No.: US 10,888,464 B2
(45) Date of Patent: Jan. 12, 2021

(54) PRESSURE SENSOR FOR MEASURING PRESSURE APPLIED BY A BANDAGE OR STOCKING

(71) Applicant: VEINSENSE LTD, Heathfield (GB)

(72) Inventor: Ejaz Huq, Abingdon (GB)

(73) Assignee: VEINSENSE LTD, Heathfield (GB)

( * ) Notice: Subject to any disclaimer, the term of this patent is extended or adjusted under 35 U.S.C. 154(b) by 0 days.

(21) Appl. No.: 16/091,422

(22) PCT Filed: Apr. 5, 2017

(86) PCT No.: PCT/GB2017/050953
§ 371 (c)(1),
(2) Date: Oct. 4, 2018

(87) PCT Pub. No.: WO2017/174984
PCT Pub. Date: Oct. 12, 2017

(65) Prior Publication Data
US 2019/0151160 A1    May 23, 2019

(30) Foreign Application Priority Data

Apr. 5, 2016  (GB) .................................. 1605817.4

(51) Int. Cl.
*A61F 13/08* (2006.01)
*A61F 13/00* (2006.01)
*G01L 1/00* (2006.01)

(52) U.S. Cl.
CPC ........ *A61F 13/08* (2013.01); *A61F 13/00004* (2013.01); *A61F 13/00017* (2013.01);
(Continued)

(58) Field of Classification Search
CPC ................ A61F 13/08; A61F 13/00004; A61F 13/00017; A61F 13/00038;
(Continued)

(56) References Cited

U.S. PATENT DOCUMENTS 3,908,645 A * 9/1975 Sandvig .............. A61F 13/0203
602/74
7,260,999 B2 * 8/2007 Divigalpitiya ......... H01H 1/029
73/774
(Continued)

FOREIGN PATENT DOCUMENTS

| GB | 2445760 A | 7/2008 |
|---|---|---|
| RU | 2003064 C1 | 11/1993 |
| WO | 2012093259 A1 | 7/2012 |

*Primary Examiner* — Octavia Hollington
(74) *Attorney, Agent, or Firm* — Saliwanchik, Lloyd & Eisenschenk

(57) ABSTRACT

A sensor suitable for measuring the pressure applied by a bandage is provided. The sensor comprises an elongate strip having a sensor region. The sensor region comprises: a base plate; a top plate; a compressible spacer positioned between the base plate and the top plate and, an electronic sensing apparatus configured to detect distance between the top plate and the base plate. The top plate is arranged to compress the compressible spacer and arranged such that the bandage exerts a force on the surface of the top plate perpendicular to the surface when the sensor is positioned between the bandage and a limb.

21 Claims, 11 Drawing Sheets

(52) U.S. Cl.
CPC ........ *A61F 13/00038* (2013.01); *G01L 1/005* (2013.01); *A61F 2013/00957* (2013.01)

(58) Field of Classification Search
CPC ........... A61F 2013/00957; G01L 1/005; A61H 1/008; A61H 9/00
USPC .......................................................... 73/774
See application file for complete search history.

(56) References Cited

U.S. PATENT DOCUMENTS

| | | | | |
|---|---|---|---|---|
| 7,854,716 | B2* | 12/2010 | Schuren | A61F 13/069 602/75 |
| 7,951,124 | B2* | 5/2011 | Boehringer | A61F 13/00021 602/43 |
| 8,448,531 | B2* | 5/2013 | Schneider | G01L 1/26 73/862.641 |
| 8,491,514 | B2* | 7/2013 | Creighton | A61L 15/58 602/60 |
| 8,894,590 | B2* | 11/2014 | Lamoise | A61B 5/103 600/587 |
| 9,204,799 | B2* | 12/2015 | Davies | A61F 13/00 |
| 10,285,867 | B2* | 5/2019 | Rapp | A61F 13/00029 |
| 2008/0306407 | A1* | 12/2008 | Taylor | A61B 5/1036 600/587 |
| 2011/0179886 | A1 | 7/2011 | Schneider | |
| 2012/0238933 | A1* | 9/2012 | Murphy | A61F 13/0273 602/53 |

\* cited by examiner

PRESSURE SENSOR FOR MEASURING PRESSURE APPLIED BY A BANDAGE OR STOCKING

CROSS REFERENCE TO RELATED APPLICATIONS

This application is a National Stage Application of International Application Number PCT/GB2017/050953, filed Apr. 5, 2017; which claims priority to Great Britain Patent Application No. 1605817.4, filed Apr. 5, 2016.

FIELD OF THE INVENTION

This invention relates to a sensor, and in particular to a device that can be used to measure pressure applied by a bandage or stocking, such as a graduated compression stocking, around a venous leg ulcer.

BACKGROUND OF THE INVENTION

Venous leg ulcers affect between 1% and 1.5% of the UK population at any given time. Based on 60 million persons, this equates to approximately 200,000 individuals with ulcers requiring treatment at any given time. Estimates of overall cost to treat range from £450 million to £800 million per year. In the USA, the estimate of cost to treat comes in at almost $5 billion per year. The average length of time any one person has an ulcer for is upwards of six months and it is not at all uncommon for individuals to have ulcers for years. If an ulcer does heal, relapse rates are commonly as high as 50% at six months, without precautionary measures.

A mainstay of treatment includes multi-layered graduated compression bandaging; using an elasticated bandage, higher pressure is exerted at the ankle, the bandage becoming progressively less compressive up to the knee. Bandaging up beyond the knee is not necessary. The application of excessive pressure can cause discomfort or actual harm to a patient, thought to occur in up to 10% of all managed cases. The application of insufficient pressure has negative consequences on the healing process, and may also provide insufficient support or fail to maintain the bandage in place. Accordingly, there is a need to apply correct graduated compression. This is a highly skilled task, e.g. requiring nurses to undertake lengthy training courses. Health care practitioners generally become competent only through many years of experience but unfortunately, even when trained and experienced, evidence suggests incorrect application of graduated compression bandages between 50-90% of the time.

Many compression bandage types exist on the market, all with different stretch characteristics, and several techniques for application exist. These factors make it exceptionally difficult to get the graduated compression profile absolutely correct, so as to maximise the chance that the ulcer eventually heals.

Individual diaphragm pressure sensors are well known and can be air-filled, water-filled, oil-filled, etc. Commercially available rigs (formas) for noting the compression ability of graduated compression socks on, for example, a test mannequin are based on a diaphragm system. However, the problem of ensuring correct usage remains.

WO2006/013422 reviews known pressure sensors, and proposes a sensor that may be placed directly on the body or between the windings of a bandage. Such a pressure sensor, for providing an indication of the pressure applied by a bandage to a human or animal body, comprises an elongate, flexible support strip adapted to be placed between a bandage and the body, the strip carrying a flat pressure-sensitive portion whose electrical properties vary with applied pressure normal to the plane of the strip, and also carrying flat, flexible conductors for connecting the pressure-sensitive portion to a supply of electricity and to means for providing an indication of the applied pressure. The pressure-sensitive portion is a Quantum Tunneling Composite (QTC), a material available in flexible form as sheets and whose conductivity changes in accordance with pressure applied across the plane of the sheet.

The use of a flat pressure-sensitive portion allows the provision of a thin strip that can be readily introduced underneath or between the windings of a bandage, and can also be removed after use. The device is however dependent on the use of a QTC material, and has disadvantages including (i) the difficulty of producing a homogeneous composite material such that the electrical response is uniform throughout the device, and (ii) the fact that the magnitude of the obtained signal from such a sensor may be low and also compromised by the level of noise, and (iii) the likelihood that incorrect measurement will be recorded if the bandage is pulled laterally across the device. In addition, if a raised area is used to obtain good results, it may be difficult to remove the device from beneath an applied bandage. Furthermore, the device may be uneconomical as a single-use, disposable product.

An alternative pressure sensor with a pneumatic operator is described in WO2012/093259 where a plurality of individually inflatable balloon sections are described coupled to a rigid strip, each balloon section acting as a sensor. The sensor array is administered under the bandage, the balloon sections are inflated and the pressure determined from the sensors. Although this system overcomes the aforementioned accuracy and single-use problems of other systems, since the system must be connected to a source of air through a volume of tubing, the sensor is potentially unwieldy, is relatively time-consuming to position and is not very easily portable. Such sensors can be prone to issues such as air leakage and hysteresis.

SUMMARY OF THE INVENTION

The present invention is based on a realisation of the need for a simple, accurate, flexible device that can aid in the application of graduated compression using bandages, to readily achieve a correct compression profile up the leg, even if applied by a healthcare practitioner with limited training. The device could be removed following correct application of the bandage(s), or could be left in situ, designed to provide on-going, real-time pressure readings over a period of time, for example one week. This could allow earlier re-application of a bandage that had worked loose during the weeks' activity of the wearer. Using telemetry, under bandage pressure data can be transmitted to a remote device such as a mobile phone to alert a healthcare provider, or an electronic storage device for future data assessment by clinicians.

In a first aspect, a sensor suitable for measuring the pressure applied by a bandage is provided. The sensor comprises an elongate strip having a sensor region. The sensor region comprises: a base plate; a top plate; a compressible spacer positioned between the base plate and the top plate; and, an electronic sensing apparatus configured to detect distance between the top plate and the base plate. The top plate is arranged to compress the compressible spacer and arranged such that the bandage exerts a force on the surface of the top plate perpendicular to the surface when the sensor is positioned between the bandage and a limb. The top plate may be a rigid top plate. Aspects of the present invention may also have utility in determining pressure beneath for example, a plaster cast being applied to mend a broken bone, or in industrial applications such as insulating paper wrapped around electrical cables.

A sensor configured in this way is both accurate and reliable but more importantly, maintains a very low profile so that it can easily be removed from between the bandage and the body once the correct pressure has been applied. The arrangement of the top plate is such that the pressure on the leg exerted by the bandage can be reliably derived from the electronic sensing apparatus.

The width of the top plate is important and may be calculated according to the equation:

$$R = (H/2) + (W^2/8 \times H)$$

where R is the radius of the limb around which the bandage is to be wrapped, H is a gap between the bandage and the centre of the surface of the top plate and W is the width of the top plate. It has been identified that the width of the top plate is key. The equation provides a configuration where the force applied by the bandage is exerted down on to the top plate as if the top plate was the limb. Therefore, the distance between the top plate and the base plate accurately corresponds to, or is substantially proportional to, the pressure exerted on the body by the bandage. When W exceeds a threshold value, the applied bandage force may be exerted on the edges of the top plate and not at the surface. As a consequence, there will be little downward movement of the top plate unless excessive force is applied by the bandage.

Preferably, the width of the top plate is less than 15 mm and thus the force is exerted down onto the top plate for all typical leg sizes. This selection is itself innovative and results in a consistent measurement from the sensor for all typical leg sizes. For a rectangular plate, the width will be 15 mm. For a circular disc shaped plate, this 15 mm dimension will be the diameter.

In one embodiment, the electronic sensing apparatus comprises a light source and an optical sensor arranged to detect light emitted from the light source. The light source may be a light emitting diode (LED) which may be printed, organic, inorganic, or otherwise manufactured. The optical sensor may be a photodiode or phototransistor arranged to receive light reflected from the underside of the top plate. Such source and sensor combinations can be manufactured cost-effectively and with a low profile which is well suited to the present application. The light source and optical sensor may be printed or can come as one package or both and may be affixed to the base plate which may house required interconnects.

Alternatively, the electronic sensing apparatus may comprise a capacitor, wherein each conductive plate of the capacitor is coupled to the top plate and base plate respectively. Such apparatus can again be manufactured cheaply and easily but requires interconnections to the top plate rather than the base plate only. In a further embodiment to this alternative, the compressible spacer maybe configured between the conductive plates of the capacitor as a dielectric. This would require careful configuration to reflect a change in distance as a change in pressure but may keep the overall thickness of the package small, preferably less than 4 mm.

In a preferred embodiment the compressible spacer may have a Young's modulus of approximately 0.4 GPa, a tensile strength in a first direction of approximately 0.3 N/mm$^2$, a tensile strength in a second direction of approximately 0.15 N/mm$^2$ and a density of approximately 20 Kg/m$^3$. The first direction may be lengthwise and the second direction may be crosswise, each direction relative to the ankle when the sensor is placed vertically upon the leg.

More preferably, the compressible spacer may have a thickness of less than 3 mm. In this way the overall thickness of the package may be small such that the package can be removed from under the bandage once the correct pressure profile has been determined. Removal may be required thereafter.

The compressible spacer may be made, for example, of foam or rubber. Alternatively or additionally, the compressible spacer may comprise a micro spring. The spring may allow for accurate configuration and. Additionally, the low hysteresis of a spring, preferably made of stainless steel provides for a fast response as the bandaging procedure is carried out and the applied pressure sensor is monitored.

The microspring may optionally be arranged to reduce tilting such that the change in the optical path length can be avoided, which may produce an inaccurate reading. The microspring may by cylindrical, conical, wave type or similar and may be arranged with a low profile to reduce the height of the sensor device. Preferably the microspring is to be fixed to the base plate and the top plate so as to leave a central region of the spring free of adhesive. In this way, interruption in the light received from the LED is lessened.

Optionally the compressible spacer may comprise a membrane or cloth attached to the edge of the top plate to shroud the spring such that the spring is shrouded with a negligible effect on the compression of the spring and the measurements of the compressible spacer.

The sensor may optionally be coated with a low friction material for safety and to facilitate removal of the sensor from under the bandage. The sensor may be spray coated, or laminated with a plastic. The coated material may also act to protect the package and enable re-use, for example it may provide for disinfecting and re-use in a clinical environment.

In certain embodiments the top plate may be rounded. The rounded shape may be configured so that the pressure is exerted by the bandage evenly and consistently. The top plate may comprise a pedestal such that when the sensor is used with particularly large limbs, the pedestal helps to reduce the width of the top plate for the bandage to make substantially contact and apply the required force.

Additionally or alternatively the base plate may be rounded such that, the sensor strip and can be easily removed without causing any damage to the leg. This may provide comfort for the patient and also may improve the reliability of the measurement. Both top plate and base plate may be rigid and thin.

Preferably the sensor may comprise a control unit. The control unit may be configured to: receive data from the electronic sensing apparatus indicative of the distance between the top plate and the base plate; and, output an indication of the pressure exerted on the sensor by the bandage when wrapped around the sensor based on the received data. The control unit may be electronic.

In this way the sensor is able to provide the clinician a reliable and accurate indication of the compression provided by the bandaging applied to the limb. The removable nature of the preferred sensor allows the sensor to be retrieved following the bandaging procedure.

In preferred embodiments, the sensor may comprise a plurality of sensor regions arranged along the length of the elongate strip. In this way graduated pressure may be detected. Moreover multiple pressures at various points can be detected. The regions may be spaced apart to provide accurate measurement at different bandage lengths or recommended clinical distances for graduated pressure. The number of sensor regions on a strip may be three or more and preferably, may be four or five.

The compressible spacer may optionally be a single piece of compressible material or may be a plurality of pads separated by a gap in which the electronic sensing apparatus is arranged. The compressible spacer of each sensor region may additionally have a circular or donut shape having a gap at the centre in which the electronic sensing apparatus is arranged. These exemplary configurations provide for reliability of measurement due to a consistent, even and predictable compression, ease of manufacture and protection for sensitive electronic configuration.

The sensor regions may be spaced apart by a flexible connector. The flexible connector thus aids conformation to the leg contour. The flexible connector may facilitate removal of the sensor from under the bandage and may also provide comfort to the patient. The flexible connector may comprise electrical connectors to the sensor regions. The flexible connector may comprise a polymer elongate strip having a thickness between, or in the region of, 50 microns to 1 mm.

In certain embodiments, the sensor may comprise a moisture resistant coating or may itself be substantially moisture resistant.

Further, a method may also be provided for testing the compression of a bandage around a limb, which comprises winding the bandage around the limb and a sensor according to any of the above aspects, the sensor being positioned along the limb and the length of the intended bandage, and determining the pressure applied to the limb at a plurality of points corresponding to the sensor regions.

DETAILED DESCRIPTION

As described above, the present invention is embodied by a sensor having a compressible spacer arranged between two plates such that force exerted on one of the plates compresses the compressible spacer and an electronic or optoelectronic sensing apparatus is able to detect the distance between the two plates. This distance can be translated into an accurate estimation of the pressure exerted on the plate and therefore, the pressure exerted on a limb at that location as a result of a bandage wrapped around a limb. For clinical purposes it would be beneficial to detect graduated pressure and so the sensor may take the form of a strip having multiple sensor regions.

The invention may also be used in wide ranging medical applications including but not limited to oesophageal pressure, bladder pressure, intracranial pressure, intraocular pressure and blood pressure monitoring. Similarly this technology will have applications in veterinary instrumentation where pressure monitoring in required.

Further applications of the invention include automotive (air bag control, tire pressure monitoring etc.) robotics, aerospace, oil and gas exploration, pharmaceutical and many other fields where high precision pressure monitoring is required, particularly but not limited to current applications where MEMS-based pressure sensing is used. This pressure sensing technology is expected to be an improved replacement for piezoresistive, capacitive, electromagnetic, piezoelectric etc. sensing technologies.

Figure 1:
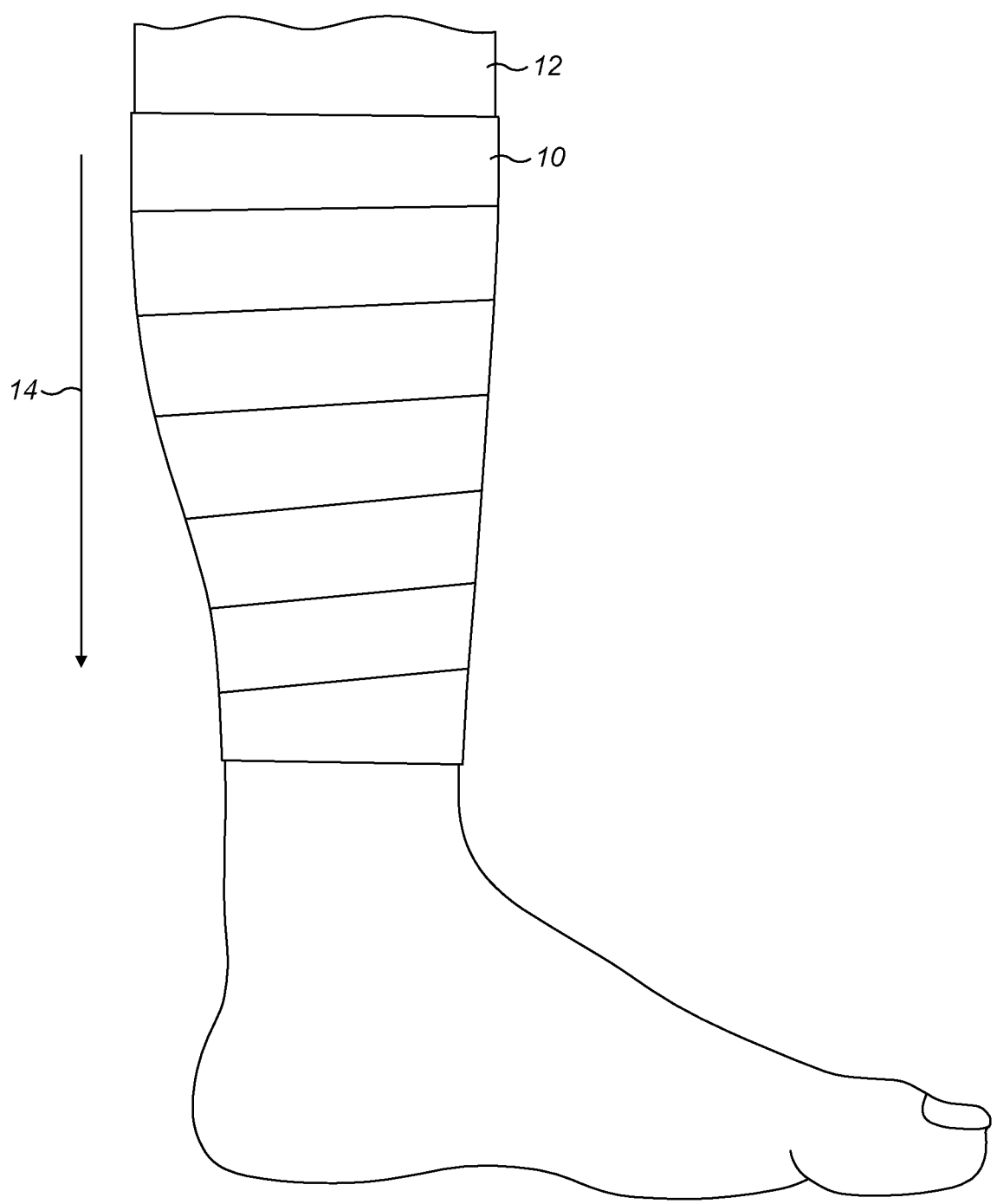
FIG. 1 is a side view of a leg illustrating a bandage exerting a graduating force on the leg.

Examples of the present invention will now be described with reference to the accompanying drawings and the application to pressure monitoring of a bandage wrapped around a limb. To provide context, FIG. 1 illustrates a bandage 10 wrapped around a leg 12. This figure is included merely to illustrate the direction of the graduated pressure, depicted here by arrow 14 with reduced pressure at the knee end and increased pressure at the ankle end.

Figure 2:
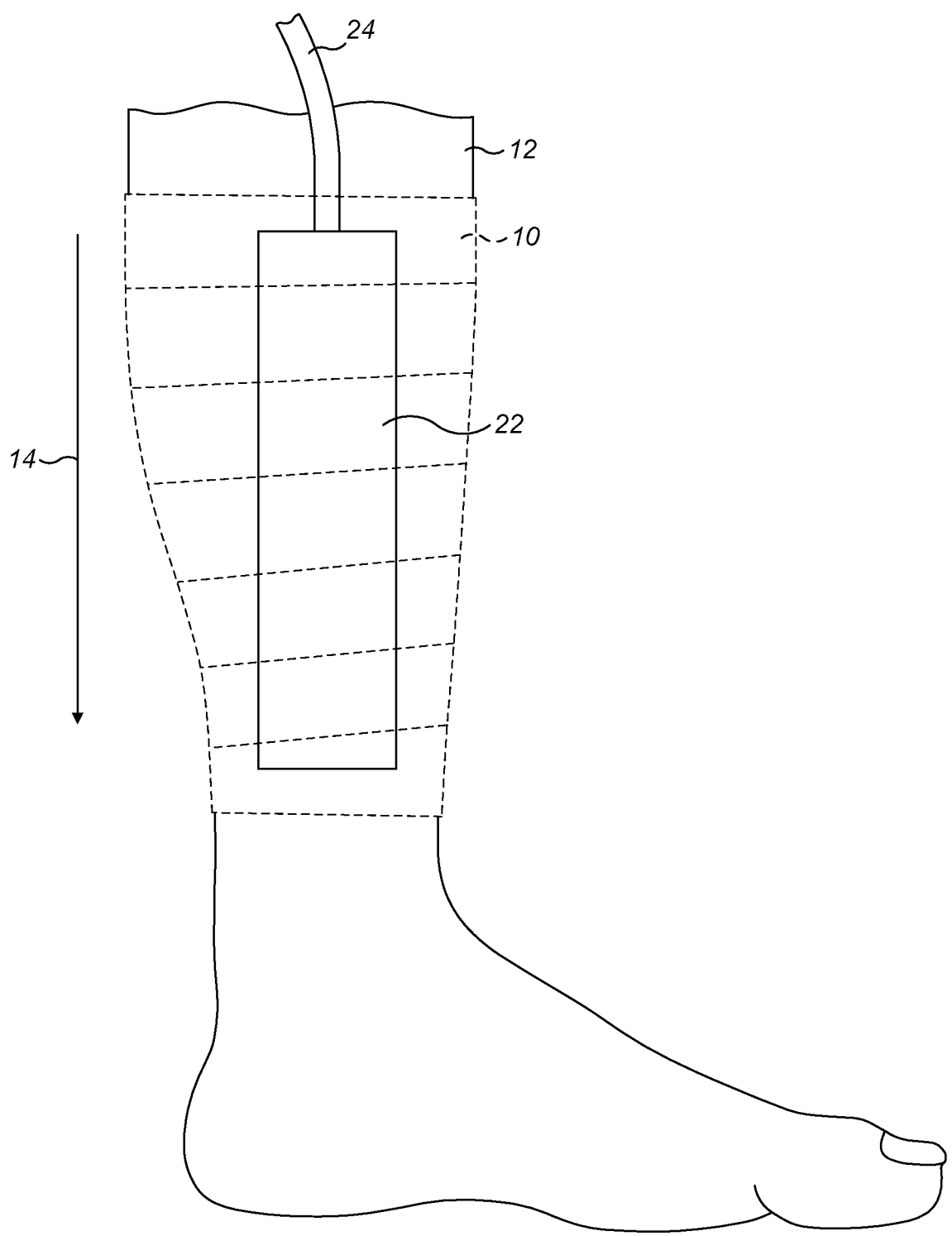
FIG. 2 is a side view of a leg illustrating a sensor strip according to the invention placed in a transverse manner to the bandage.

Typically the lower limb of a patient with an area of (venous) ulceration suitable for graduated compression bandaging (using either two-layer, three-layer or four-layer systems and as part of routine clinical management) has the ulcer site cleaned and topically dressed. Next, typically, a layer of padding is wound gently around the lower limb, such as Velband™, to act as both an absorbent layer (should the ulcer be exudative) and to provide additional comfort to the patient's leg prior to compressive bandages being applied. As illustrated in FIG. 2, a sensor strip 22 of the invention is positioned underneath the bandage 10 relative to the leg 12. The sensor 22 is placed vertically, lying either on the outer (lateral) aspect of the calf, such that its lower aspect is slightly above the level of the upper part of the lateral malleolus (outer part of the ankle 'bone'), or on the inner (medial) aspect of the calf, such that its lower aspect is slightly above the level of the upper part of the medial malleolus (inner part of the ankle bone). Bandaging commences from the forefoot, passing up towards the knee, in one of several standard fashions, and over the sensor. Two, three or four layers of bandaging are applied—the bandages are generally heavily elasticated. Ideally, the bandages are applied such that the pressure sensor level at the ankle will be recorded as approximately 40 mmHg declining to approximately 20 mmHg just below the knee or other combinations of high and low pressures as prescribed by the clinician—with a progressive and steady fall of pressures sensed in the interval between, to provide 'graduated' compression moving up the calf. The pressure sensor may require an accuracy (tolerance) of approximately +/−2 mmHg. The sensor 22 is connected to a display or computer unit through a wired or wireless connection 24.

The length of the sensor strip should ideally be long enough in order to detect sufficient graduated pressure along the length of the leg from the ankle bone to just below the knee. Obviously, as leg lengths vary, for varying lengths of sensor strip may be required. This might mean on the longer strips the strip may include 4, 5 or more sensor regions. A design consideration includes whether or not the strip can removed after single use, or such that it stays in situ beneath the bandaging for a week, depending on the clinician's recommendation. An exemplary length of 300 mm may be selected for this purpose.

Figure 3:
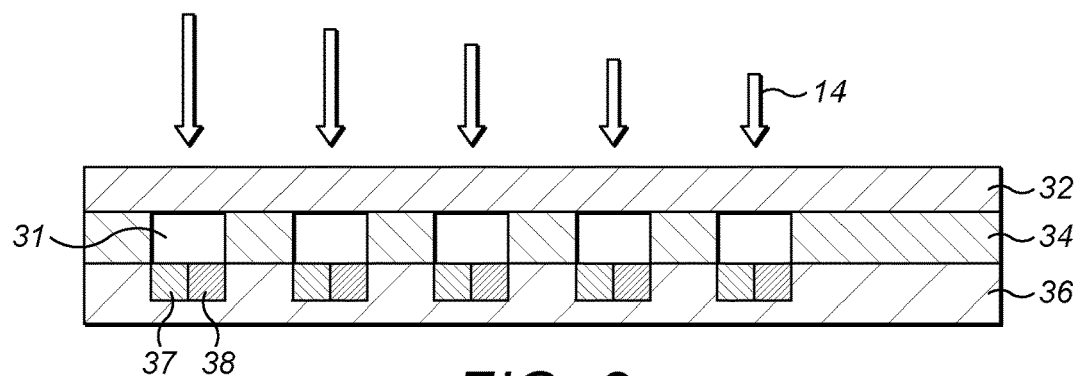
FIG. 3 is a schematic cross-sectional view of a sensor embodying the present invention.

FIG. 3 illustrates a schematic cross-section of an exemplary architecture of a sensor strip. As in FIGS. 1 and 2, the graduated force is illustrated by arrows 14. The sensor is designed such that a compressible spacer 34 separates a top plate or force bar 32 from a base plate or substrate 36. When the force 14 is exerted on the top bar, the compressible spacer 34 is compressed and the distance between the top plate 32 and the substrate 36 is reduced. The sensor strip includes a plurality of gaps 31 in the compressible spacer and arranged in the gaps in one example is a light source and a light detector. In this example light is emitted by the light source 37 and reflects off the top plate to be received by the light detector 38. As the distance between the top plate 32 and the base plate 36 is reduced, the intensity of the light increases and the changing distance can be detected. Since the force applied on the top plate is graduated, as illustrated by the arrows 14, the distance between the top plate and the base plate 36 will be different in each gap and therefore, the amount of light sensed by the light sensor 38 will be different within each gap or sensor region. Accordingly, the graduated pressure can be detected along the length of the strip.

In the illustrated embodiment of FIG. 3, the base plate 36 may include a transducer substrate and interconnects such that the light source can receive power to emit the light and the light detector may pass its readings to a suitable computing or data storage apparatus. In the embodiment illustrated, the top plate or force bar 32 may also include a light reflector positioned on its underside. The plate may also be made of a suitable light reflective material. For example, if the light source (e.g. LED) is an infrared device then this plate may be opaque and white. If visible light is used as a light source then the plate may be matched to the colour of the wavelength of light used. If for example red light is used, then the plate may be opaque red. The width of any reflecting arrangement positioned on the underside of the plate 32 may be matched to the width and length of the overall plate upon which the force is exerted.

In one example, a combination of a light emitting diode (LED) and a photo transistor is used as the light emitting device and light receiver. The LED may be infrared or visible light. The preferred material and method of manufacture would be an inorganic LED which has been printed. However, it is contemplated that the device may be manufactured using more conventional semiconductor fabrication techniques and inorganic materials will also be feasible. In order for the sensor to be inserted underneath the bandage, detect the pressure and be removed easily, the overall package should have a low thickness profile. To achieve this, a LED and receiver with a small height would be preferable.

The compressible spacer 34 positioned between the top plate 32 and the base plate 36 could be made of a variety of materials, such as foam rubber and may be adhered to the top plate using glue. To keep the overall profile of the device low, to facilitate easy retrieval of the device following the bandaging procedure, the thickness of the foam should be small, ideally less than 2 mm. The compressibility or modulus of the foam (or similar material) should be such that when the force is applied to the top plate by the bandage, the corresponding pressure at the bottom surface, directly underneath (for example where the optical device is positioned) should be 40 mmHg, or as prescribed by the clinician. Additionally, this functions to reduce the gap between the top of the optical device and the bottom of the top plate to under 1 mm and optionally 0.5 mm. It is to be noted that 40 mmHg to 60 mmHg is currently the highest pressure applied on any leg ulcer bandaging procedure.

The spacer compressibility is important. If the spacer is too rigid, excessive force from the bandage may be required to move the top plate downwards. This means that the distance between the two plates (top and bottom) will not be reduced significantly for the sensor device to register change, while excessive force is being applied to the leg. Conversely, if the spacer is too soft, very little bandage force will cause the distance between the two plates to reduce, and insufficient pressure will be applied to the leg. Therefore, the compressibility of the spacer could be proportional to the required pressure on the leg and at the same time providing adequate distance change between the plates for the sensor to easily respond.

The distance between the bottom of the top plate and the light source and receiver will be configured according to the characteristics of the particular source and receiver combination. For example, when using a device like the GP2S60 manufactured by Sharp™, the maximum current is obtained at the output of the photo transistor at a distance of 0.5 mm.

Turning now to discuss the characteristics of the top plate 32, this top plate is preferably a rigid plastic 'force bar'. Exemplary measurements of the plate may be approximately 300 mm in length and 10 mm in width and 1 mm in thickness. These measurements have been selected such that the force, and pressure, is applied evenly during bandaging. The plate should ideally have non-sharp edges.

It has been identified that the width of the plate is important when the sensor is placed vertically, lying on the inner or outer aspect of the calf. The bandage is preferably in contact with the surface of the force bar and not the edge of the force bar when in use. Correct force will not be applied if the bandage is not in contact in with the surface of the force bar, in which case the applied force will be at the edges of the sensor and not in the central region which is required in order to compress the compressible spacer in a manner such that the pressure applied on the leg can be effectively determined. This is illustrated in FIGS. 4 and 5.

Figure 4:
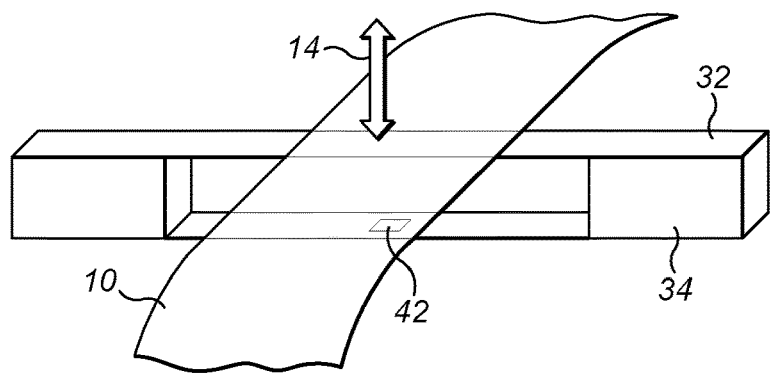
FIG. 4 is a cross-sectional view in three dimensions of a sensor embodying the present invention illustrating the bandage exerting a force on the sensor arrangement.

In FIG. 4, the optical sensor and receiver 42 are shown centrally. The force 14 is illustrated to be applied centrally on the force bar such that when the force bar is depressed and the compressible spacer is compressed either side of the air gap, the distance between the force bar and the sensor is changed in the corresponding manner to the pressure applied by the bandage.

Figure 5:
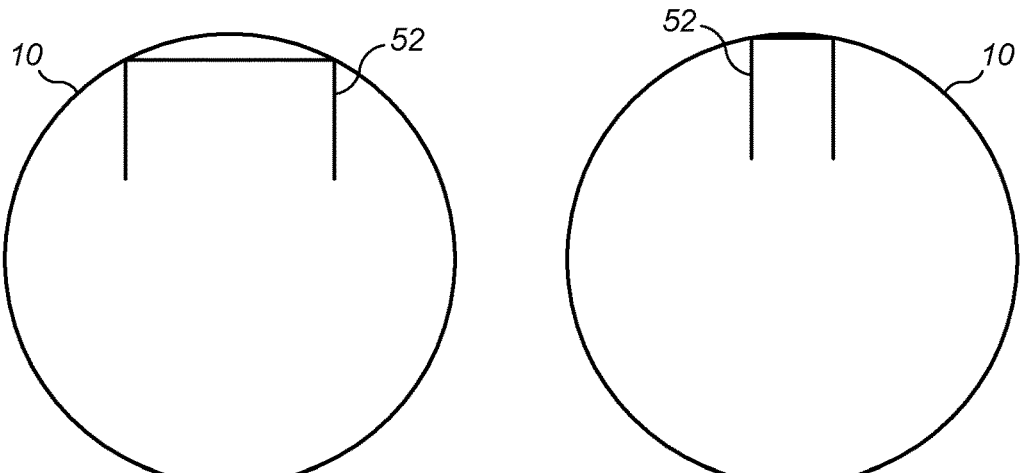
FIGS. 5, 6 and 7 are cross-sectional views of a bandage wrapped around a dummy leg illustrating force exerted on the sensor arrangement when in position.

FIG. 5 illustrates a bandage 10 wrapped around a dummy leg. The top plate is illustrated by item 52. In the left hand image, poor contact is made between the bandage and the top plate such that the force exerted on the top plate will not depress the top plate in a manner consistent with the pressure applied by the bandage on the limb. In the right hand image, good contact is made between the bandage and the surface of the top plate, a sufficient vertical force is applied, and the force and pressure detected by a changing distance of the top plate can be measured effectively corresponding to the pressure applied by the bandage on the limb.

Compression bandages are typically specified according to the ankle diameter of the leg to be bandaged. For instance, if the ankle's circumference is 18 cm the bandage may be specified as producing a pressure of 40 mmHg on the ankle when it is stretched by 50%. In order to effectively determine the width of the top plate or force bar a calculation may be used as follows:

$$R = (H/2) + (W^2/8 \times H)$$

where R is the radius of the ankle;
H is the gap between the bandage and the top of the top plate or force bar; and,
W is the width of the top plate when the top plate is placed vertically along the leg.

Figure 6:
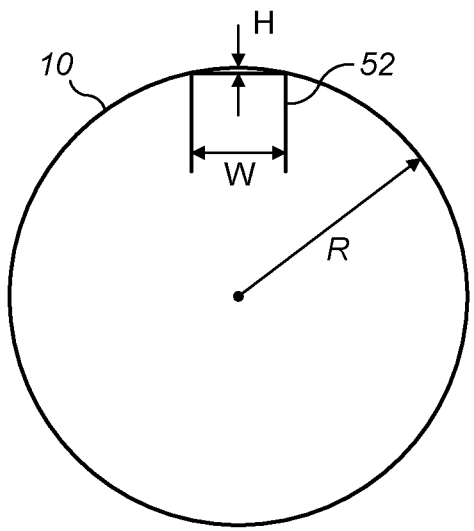

FIG. 6 illustrates these variables on the previously illustrated dummy leg. Again, the bandage placed around the ankle circumferentially is illustrated by item 10 and the top plate is illustrated by item 52. The variables of the equation R, W and H are illustrated such that the equation can be more easily understood.

If a wider top plate is required to cover a wider (transverse) area of the leg to be bandaged, it is envisaged that an additional feature of the top plate may be provided such that appropriate contact with the bandage can be established. As above, appropriate contact between the bandage and the surface of the top plate is required such that the pressure exerted on the top plate may be equivalent to the pressure exerted on the leg when the bandage is in use. This contact enables the pressure to be exerted evenly across the plate and in a vertical direction or a direction substantially perpendicular to the surface of the top plate.

Figure 7:
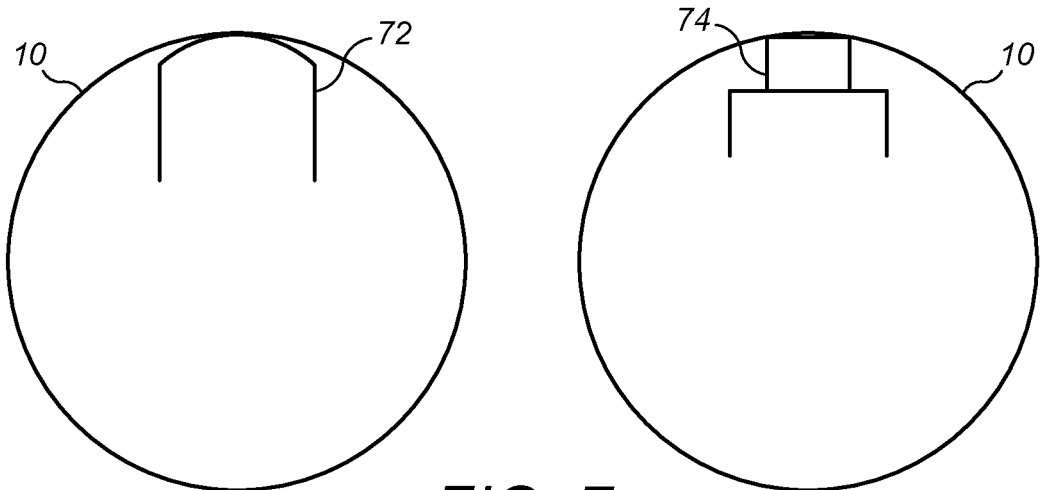

Exemplary additional features to provide this contact are illustrated in FIG. 7. On the left hand side, the bandage 10 is again illustrated. A rounded top plate is illustrated which enables bandage contact to be improved. Should the top plate be rounded, the curvature of the plate may be fixed, or may be substantially flexible to cooperate with the bandaging or the curvature of the leg. The curvature may be such that the plate substantially conforms to the shape of the leg when positioned under a bandage. Since the bandage is flexible, all three elements may have substantially the same curvature which may enable the force to be evenly distributed.

On the right hand side of FIG. 7 is illustrated a further example in which a pedestal is provided on the top plate. This may be used when the sensor is used with a larger leg or limb. The pedestal enables a one size fits all sensor to be provided whilst appropriate force and contact is maintained such that the pressure exerted on the leg can be effectively measured by the sensor when positioned in place. The pedestal can be structured on the top plate. It may be detachable to enable clinical use with all types of patients.

Above, the characteristics of the top plate have been described. The characteristics of the base plate or substrate 36 will now be described. The base plate or substrate may be a rigid plastic strip which houses the optical devices and interconnects. The strip width and length should be matched to the width and length of the top plate and the thickness should be small to facilitate removal of the device when positioned under the bandage. This thickness may for example be up to 1 mm. In order to facilitate connection to the sensors, the base plate may comprise contact lines which may be metal traces provided preferably by a printed method (e.g. inkjet, screen printing). The contact lines may connect to a set of pads for connection to an external control and display unit. Although it is described that the base plate may be rigid in order to facilitate consistent measurement of distance between the base plate and the top plate, the base plate may be combination of rigid and flexible regions (illustrated in FIG. 11) such that the rigid region performs the same function as before while the flexible region allows conformity to the limb contour upon which it is to be placed. The flexible region also comprises metal line connections to the sensors. Although a printed method is described, it will be understood that any method of providing connection to the sensors is contemplated such as physical wires or other known printed circuit board or connection techniques.

Figure 8:
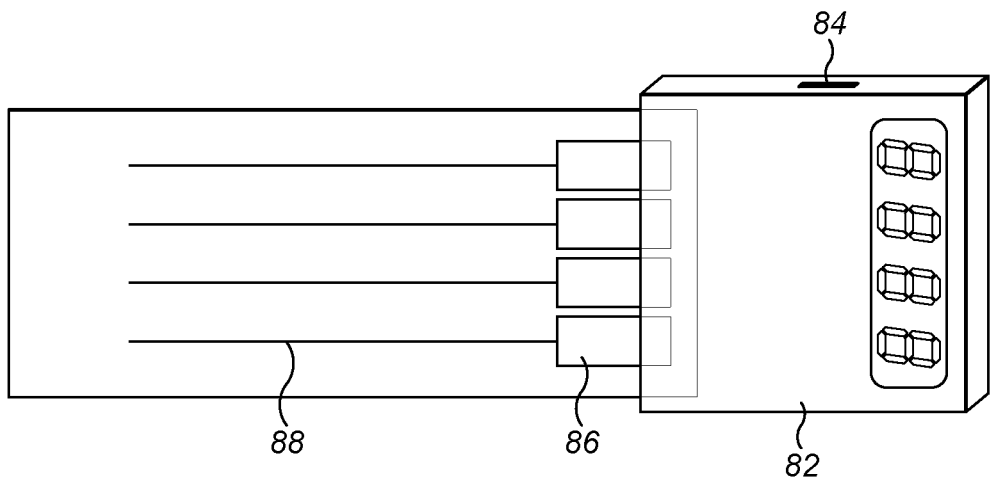
FIG. 8 illustrates an exemplary connection and display apparatus.

An example base plate is illustrated in FIG. 8. In FIG. 8, contact lines 88 are connected to pads 86 which in turn connect to a removable control and display unit 82.

The control and data unit 82 contains functions for sensor actuation and data collection, data storage, data display, data transmission and power supply. In an example, the control and data unit may comprise a display and a USB port 84 for manual data download. It is also envisaged that the control and display unit may comprise a variety of display methods such as LCD or other display or a simple traffic light system which displays that the pressure has reached the correct amount. Optionally, the control and data unit may comprise wireless connections such as Bluetooth in order to transmit data to a remote site for analysis and/or data storage.

A variety of control and data unit types are contemplated but what is important is that the data received from the electronic or optoelectronic sensing apparatus is translated into an indication of the pressure applied. For example, the unit could be provided by a laptop, PC, smartphone, or any known computing technique.

To accommodate varying graduated compression profiles (as many patients cannot tolerate 40 mmHg or 50 mmHg) the control and data unit may be operable to have a variety of pre-set graduated compression profiles set, or may have an interface to enable detection of any specific pressure. For example, the system may need to set a level from 25 mmHg just above the ankle down to 15 mmHg, or from 20 mmHg down to 12 mmHg just below the knee. The software is operable to allow for this. The operator must be able to 'dial in' a considered profile prior to use of the system.

The following is an example for the purposes of explaining the invention embodied by the control and data unit and one skilled in the art would be aware that the components of such a system may differ depending on requirements and user preference. The computer system comprises one or more processors connected to a system bus. Also connected to the system bus is working memory, which may comprise any random access or read only memory (RAM/ROM), display device and input device. A user may interact with a user interface using input device, which may comprise, amongst others known in the art, a mouse, pointer, keyboard or touch-screen. If a touch-screen is used display device and input device may comprise a single input/output device. The computer system may also optionally comprise one or more storage devices and communication device, which may enable communication over a network (non-shown). Storage devices may be any known local or remote storage system using any form of known storage media.

In use, computer program code is loaded into working memory to be processed by the one or more processors. An operating system (OS) is optionally loaded into memory together with optional computer-program code for implementing the control and data unit. Working memory also comprises computer-program code for implementing a user interface. The system may be implemented using library components. The OS and/or the computer-program code may comprise suitably configured computer program code to enable the proper functioning of the computer system as described above.

Those of ordinary skill in the art will appreciate that the processes of the present invention are capable of being distributed in the form of a computer readable medium of instructions and a variety of forms and that the present invention applies equally regardless of a particular type of signal bearing media actually used to carry out distribution. Examples of computer readable media include recordable-type media such as floppy disks, a hard disk drive, RAM and CD-ROMs as well as transmission-type media such as digital and analogue communications links.

Generally, any of the functionality described in this text or illustrated in the figures can be implemented using software, firmware (e.g., fixed logic circuitry), programmable or non-programmable hardware, or a combination of these implementations. The terms "component" or "function" as used herein generally represents software, firmware, hardware or a combination of these. For instance, in the case of a software implementation, the terms "component" or "function" may refer to program code that performs specified tasks when executed on a processing device or devices. The program code can be stored in one or more computer readable memory devices. The illustrated separation of components and functions into distinct units may reflect an actual physical grouping and allocation of such software and/or hardware, or can correspond to a conceptual allocation of different tasks performed by a single software program and/or hardware unit.

The sensor strip may optionally be left in situ, for example for one week in order to detect a change in pressure over time, likely to be a lowering of pressures as the bandage loosens with wear and activity of the patient. In this scenario, the sensor strip should be flexible enough to conform to the patient's leg, for comfort. The sensor might also need to be able to resist moisture—if the ulcer is exudative. The control and data unit may be configured to sample the data for example every hour, both day and night for that week long period, and to provide configurable options to the clinician. Data must be able to be stored and sampled at any time—if the nurse or doctor visits and the control and data unit may provide an interface to enable this to be enacted.

Further the control and data unit may allow for data to be retrieved at any time for example by the patient and transferred to a healthcare professional so that an accurate determination of whether the graduated pressure profile is maintained. If not maintained, the bandaging will be sub-optimal and will lengthen the ulcer healing process. This transfer may occur via the internet through a dedicated interface, or by conventional transmission methods such as email, SMS or USSD or other 'machine to machine' technology. The control and data unit may include a Wi-Fi interface or cellular data communication module and may also utilise a gateway or third party device to send the information to a device such as a laptop connected to the unit. To maintain optimised healing, the detection of a bandage whose pressure profile has changed would allow that bandage to be rewound or replaced—perhaps around the same sensor—which therefore, becomes semi-disposable.

In preferred embodiments, the electronic control unit is a wearable control unit and may be contained in a small footprint box (made of a flexible polymeric material such that it causes no discomfort to the patient) and placed at the end of the sensor strip and configured such that data can be received from the sensors and stored in the control unit over a period of time such as a week. The control unit may comprise a power supply, data logging facility and also, telemetry for transmitting data to an electronic device located at a remote location. Thus, this sensing technology is able to monitor likely loosening of the bandage during the course of week. This will allow improved treatment in a new way, such that the desired compression profile is always maintained.

In a preferred embodiment, the 'wearable control unit' is designed in such a way, as not to cause any discomfort for the patient over the course of placement in situ, for example, for one week.

As has been described above, one example of an electronic sensing apparatus uses optoelectronics in order to emit light which is reflected off the top bar (or sent directly to) a light source where the intensity of the light corresponds to the distance between the top and base plates which can then be translated into a pressure measurements once the characteristics of the compressible spacer are known. However, any known electronic sensing apparatus that is able to detect the distance between the two plates can be used. Examples include capacitive sensing, magnetic sensing, inductive sensing, resistive sensing, and electrostatic sensing. In these embodiments a matrix of sensors may be used to detect pressure at multiple locations along the strip in a similar manner to the way touch is detected on a touch sensitive display.

Figure 9:
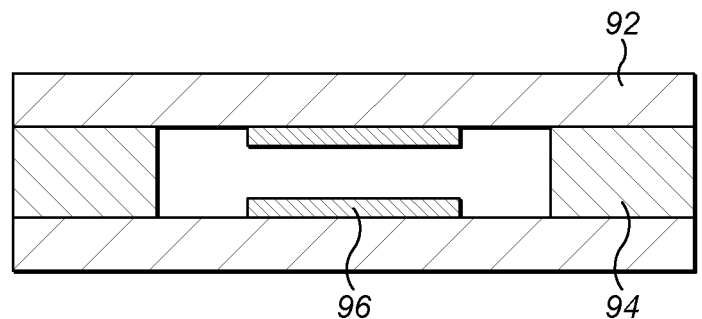
FIGS. 9 and 10 are schematic cross-sectional views of exemplary sensors.
Figure 10:
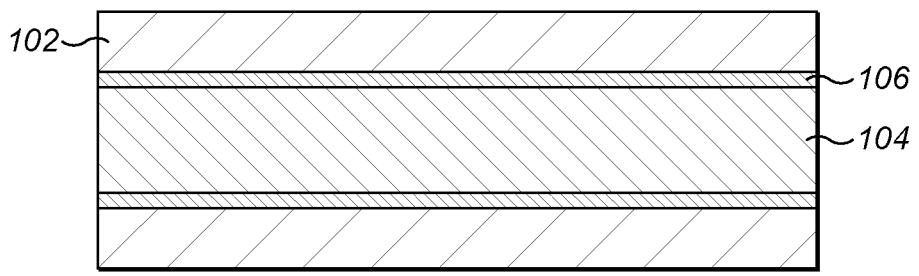

Examples in which a capacitive sensing means is used are illustrated in FIGS. 9 and 10. In FIG. 9, two conductive plates of a capacitor are coupled to each of the top plates 92 and base plate respectively. As the compressible spacer is compressed upon pressure applied to the top plate, the distance between the two conductive plates is reduced. The capacitance is varied and therefore changing distance detected. From the characteristics of the capacitor and the characteristics of the compressible spacer, the distance between the capacitor plates can be translated into a pressure measurement exerted on the top plate and therefore the pressure exerted by the bandage on the limb.

In the embodiment illustrated on FIG. 9, the dielectric of the capacitor is an air gap created by gaps in the compressible spacer. Although it is described that the compressible spacer may be a single compressible spacer with gaps, it will be understood that the plates may be separated by multiple compressible spacers or pads separated from each other by a gap.

In the embodiment illustrated in FIG. 10, the dielectric of the capacitor may be the compressible spacer 104. In this way a single compressible spacer may be used along the length of the strip. Gaps may also still be maintained in the compressible spacer in order to minimise interference between the sensing regions. The characteristic of the compressible spacer may be used to calculate the capacitance characteristics which can be used to detect the distance between the two plates and thus accordingly the pressure exerted on the top plate and hence the pressure exerted on the leg.

Figure 11:
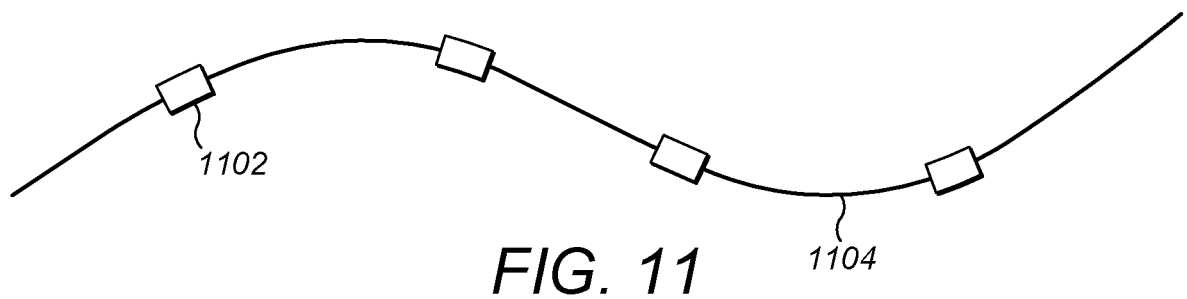
FIG. 11 is a plan view of an exemplary sensor strip.

It has previously been described that the sensor strip or sensor may be a single continuous strip with a plurality of gaps. Alternatively, the construction of the sensor may be a plurality of sensor islands mounted on a connector. For the purposes of this discussion this will be referred to as the flex-rigid design. This flex-rigid design construction comprising a plurality of sensor islands is illustrated in an exemplary manner in FIG. 11. In the illustration of FIG. 11, the sensor islands are shown as 1102 and the flexible connection strip as item 1104. Each sensor island may comprise an optical sensor combination as described above however of course a variety of different sensors is contemplated. In this example, the sensor islands are mounted on a rigid plastic or small (10 mm diameter for example) circular printed circuit board, with a rigid disc on top, the two separated by a compressible spacer made of foam or similar and spaced approximately 4 cm apart. Connections to the sensors may be printed on thin flexible plastic. The flexible construction may allow a sensor strip to conform to the leg profile. Should thickness of the sensor be less than 2 mm, easy retrieval is facilitated following the bandaging procedure.

Figure 12:
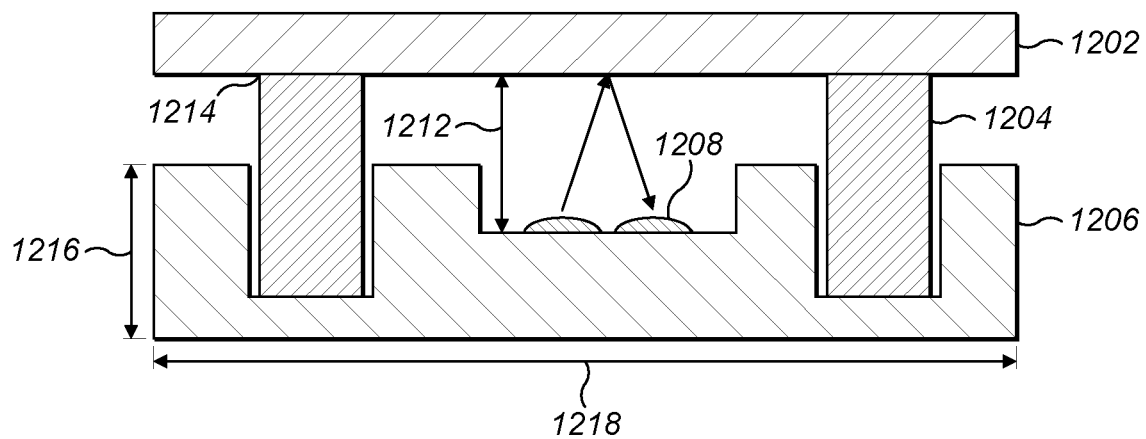
FIG. 12 is a schematic cross-sectional view of an exemplary sensor.

An exemplary individual sensor island is illustrated in FIG. 12. The top plate 1202 is separated from a rigid plastic base plate 1206 or printed circuit board. A foam spacer 1204 is positioned between the two and is coupled to the top plate by glue 1204. The electronic sensing apparatus in this example is an LED and photodiode 1208. Light is reflected from the LED and received at the photodiode 1208. The height of the base plate 1206 may be 1 mm 1206. FIG. 12 is a cross-section lengthways in which the width 1218 may be 10 mm. As above, the characteristics of the LED and photodiode will affect the distance between the base plate and the top plate along with the characteristics of the foam spacer. In this specific example, the distance 1212 may be 1 mm such that when the top plate 1202 is moved closer to the base 1206 the light reflecting off the reflective under surface of the top plate and received at the photodiode gives an effective reading at the control and display unit.

In the areas between sensor regions or areas, a means to fix the sensor in place may be included (not shown), for example medical sticky tape, medical grade glue etc. such that the strip is held in place whilst the bandage is wound around the limb.

Figure 13:
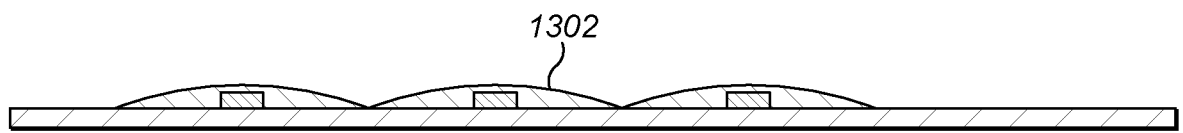
FIG. 13 is a schematic cross-sectional view of an exemplary sensor strip.

Finally, it is envisaged that the sensor strip may be covered with a top 'smoothing layer' 1302 either by spray coating or lamination at a plastic material or similar to facilitate easy retrieval, as illustrated in FIG. 13.

A particularly preferred construction is a sensor of the flex-rigid construction of FIG. 11 where the interconnects between the sensor regions are configured on ultrathin flexible substrate (e.g. 50 micron plastic) so as to conform to the limb contour. The sensor regions are constructed on 10 mm diameter islands comprising the top plate, the spacer and the bottom plate which itself comprises the sensors.

DETAILED EXAMPLE

Figure 14:
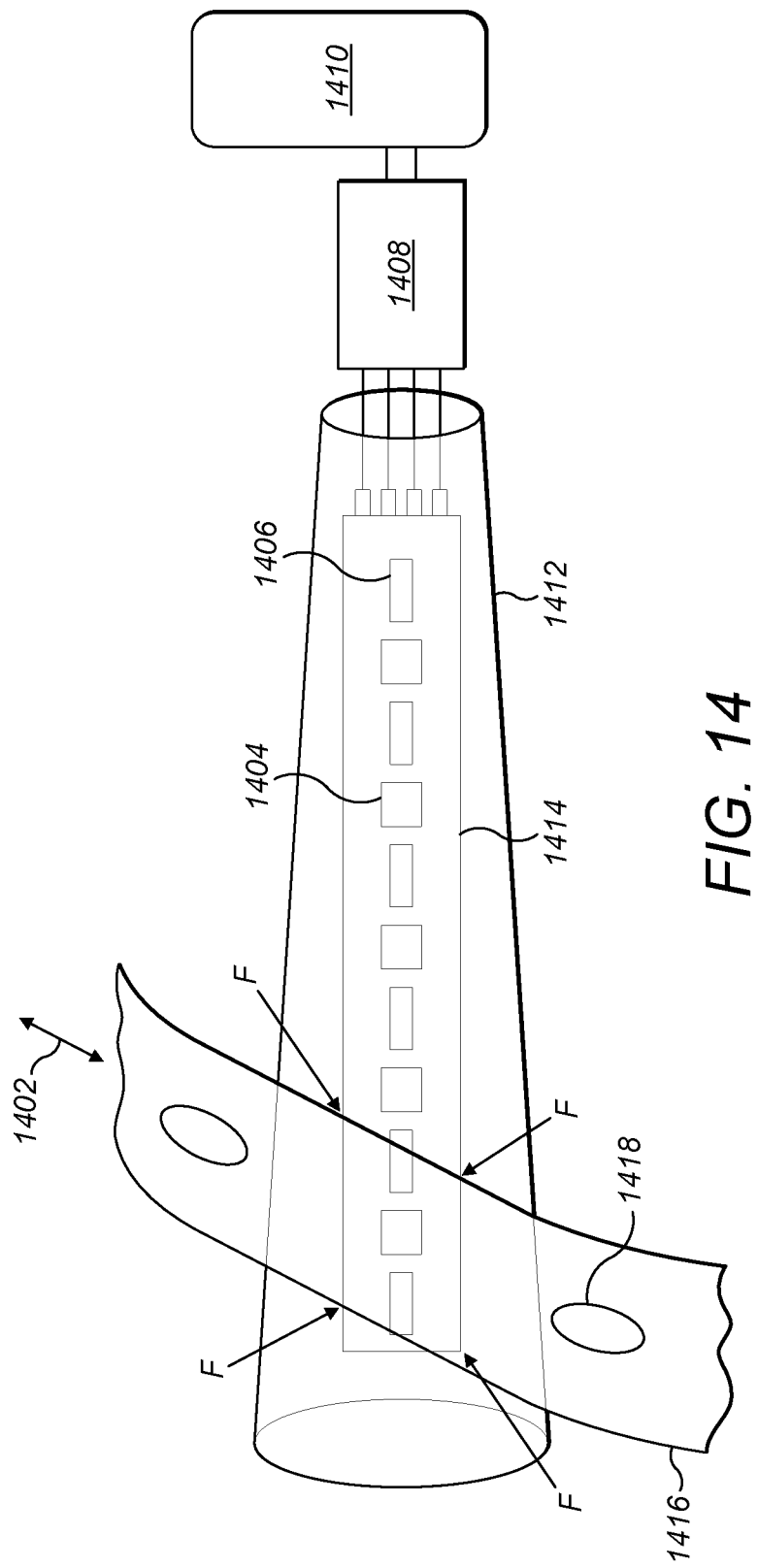
FIG. 14 is schematic plan view of a system for using an exemplary sensor.

In order to demonstrate the utility of the proposed sensor, a detailed example is considered and explained below with reference to FIG. 14. It will be noted that any requirements herein are merely exemplary and used for experimentation. A sensor strip 1414 is constructed according to the sensor illustrated in FIG. 3. A commercial, low profile, LED phototransistor (combined device TRCT1000 from Vishay™ with a footprint of 7 mm (L)×4 mm (W)×2.5 mm (H)) may be used as the sensing 1404 and receiving devices 1406. These devices may be mounted on a custom design printed circuit board 15 mm wide. For the top plate a thin (0.5 mm) rigid white plastic strip is used. The strip width is 15 mm. For the purposes of this example, a particular type of foam is selected, available from QA solutions Limited™. The foam has a tensile strength (lengthwise) of 0.3 N/mm$^2$ and the foam material has a Young's Modulus of 0.4 GPa. A programmable Arduino™ 1408 and laptop 1410 is used to operate the optical devices. To test the sensor a dummy wooden leg 1412 is manufactured. The sensor strip 1414 is placed on the dummy leg 1412 and connected to the programmable Arduino™ and laptop 1410 as shown in FIG. 14. A software program is written specifically to detect the distance and calculate the pressure measurement. As shown in FIG. 14, a compressible bandage 1416 from KTwo™, 100 mm wide is wrapped around the sensor strip 1414 according to a modified La Place equation:

$$P = T \times n \times \frac{4620}{C} \times W$$

where P is the exerted pressure on the leg in mmHg;
W is the width of the bandage in cm;
n is the number of bandage turns;
T is the tension in the bandage in Kgf;
C is the circumference of the leg in cm; and,
4620 is derived from the conversion of the unit of measurement.

With some commercial compression bandages such as the one used here, there are 'marks' 1418, such as an ellipse on the bandage at regular intervals. When the bandage is stretched 1402 by approximately 50%, the ellipse turns into a circle indicating that there is sufficient tension (t) in the bandage which when applied to the leg will produce a pressure (p) depending on the circumference (c) on the leg (at the point of application) according to the above equation.

Should the width of the top plate be wider than 15 mm, when the bandage is wrapped around the dummy leg 1412, using 50% stretch, it can be noticed that there is no movement of the plate in the vertical (downward) direction and no current recorded at the output of the phototransistor. Even when the stretch is increased to 100% there would be no movement of the force bar. This is because all the forces (F) produced by the stretchy bandage are acting at the edges of the plate.

The width of the top plate at 15 mm is calculated from the equation identified previously for a leg circumference of 18 cm. Typically adult legs range from 18-24 cm at the ankle and these numbers are used by bandage manufacturers when designing compression bandages.

As described, for the bandage to be fully in contact with the surface of the top plate, the top plate width should be less than or equal to 15 mm. Thus in this specific example the top plate is made 300 mm long and 15 mm wide.

The example KTwo™ bandage is wrapped around the dummy leg at the lower end of the leg where the circumference of the leg is 18 cm. According to the manufacturer, if c is 18 cm, when the bandage is stretched by 50% the exerted pressure on the leg should be 40 mmHg. There will of course be a small error due to the thickness of the sensor strip, which must be taken into account. However, as mentioned, the thickness of the strip is preferably no more than 2 mm or as close to this thickness as possible to minimise, absolutely, this potential small error.

As the bandage is wrapped (50% stretch—ellipse turning into a circle) the top plate is seen to move downwards in proportion to the applied force. This is clearly recorded by the rise in the output current in the phototransistor and displayed on a monitor.

In summary, this detailed example demonstrates that characteristics of the sensor must be configured in order to effectively translate the force applied on to the top plate of the sensor to a force applied by the bandage on the leg. Specific characteristics and requirements are for example:

1. There is a limiting width for the top plate above which all the forces produced by the stretchy bandage will not result in the vertical movement of the plate.

2. The spacer compression, i.e. the Young's Modulus of the spacer material, is important. The compression must be proportional to the applied force created by the bandage and also proportional to the output current from the sensor.

3. The spacer thickness is very important. To keep the overall thickness of the sensor strip thin for ease of retrieval following the bandaging procedure, the vertical separation of the sensing elements (in this case, the distance between the top of the optoelectronic device and the top of the reflector) must be low, ideally less than 2 mm. Therefore, the spacer thickness should not exceed 2 mm.

4. To reduce the thickness of the sensor strip even further, to obtain more accurate results, ideally very low profile printed optoelectronic devices such as organic LED's would be used. The lower the thickness of the sensor strip the easier it will be to remove it and without any loss of bandage pressure.

Above, it is described that the compressible spacer may be formed of foam or similar material to separate a reflector and flexible substrate such that when the reflector is depressed the distance between the reflector and substrate is reduced. As the foam compresses an optical device arranged between the reflector and flexible substrate varies its reading in a proportional manner to the varying distance between the reflector and substrate. In an embodiment, metal compression springs may be ideal to act as the spacer between the substrate and reflector.

In this embodiment, where specific configurations have been mentioned above, similar considerations and configurations may be applied.

The springs have very low hysteresis therefore one can expect fast response as the bandaging procedure is carried out and the applied pressure is monitored. In particular, stainless steel would be a preferred material. Advantageously, there would be one spring per sensor device. The spring may have a low profile (microspring) to reduce the overall height of the sensor device. Optionally, the springs can be different shapes such as a cylindrical spring on 1501, as illustrated in FIG. 15 or a conical spring 1601, as illustrated in FIG. 16, or a wave-type spring etc (not shown).

Figure 15:
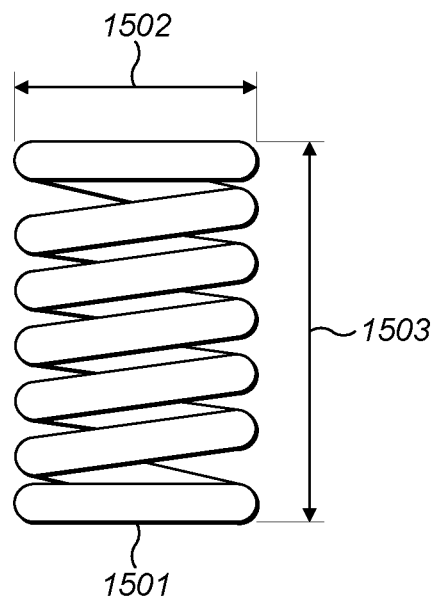
FIG. 15 illustrates a cylindrical spring.
Figure 16:
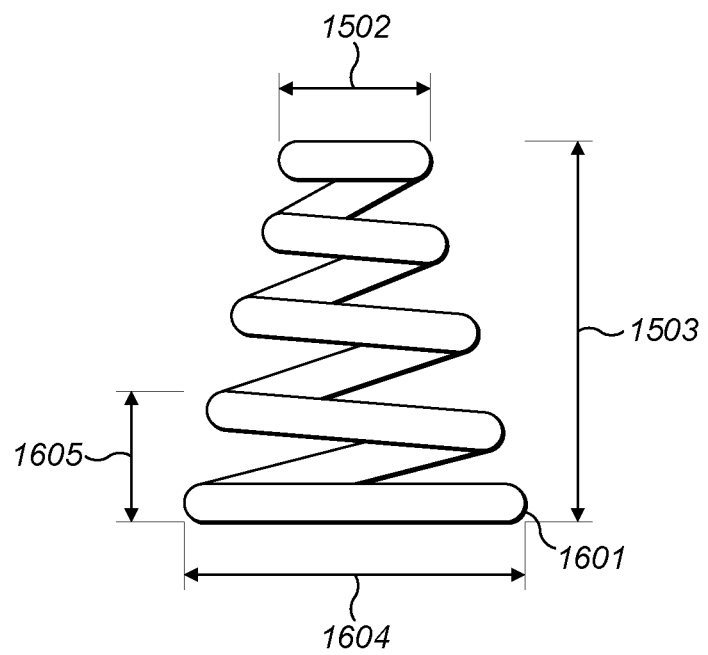
FIG. 16 illustrates a conical spring.

Microsprings should have dimensions as shown in FIGS. 15 and 16 for cylindrical and conical shapes respectively. For cylindrical springs, the length or free length 1503 should ideally be below 5 mm and the inner diameter on 502 should be in the region of 12 mm. For conical springs, as shown in FIG. 16, the free length 1503 should be less than 5 mm, the inner diameter 1502 around 5 mm, the outer diameter 1604 less than 12 mm and the maximum solid height 1605 should be no more than 0.5 mm.

An important consideration for the spring design is the spring rate. The spring rate must be such that there should be a linear response (reduction in free length 1503 as the weight (directly put on the top plate) is increased from 10 g to 150 g). This will cover the pressure range of interest under the spring (10 mmHg to 100 mmHg), applicable for venous leg ulcer management. This should be achieved within approximately 2 mm of the spring compression from its original position.

Every spring has a spring constant or a spring rate. To compress a spring to travel a millimetre of distance, expressed as $F=kx$ where F is the applied force in newtons, x is the distance in millimetres and k is the constant. For bandaging pressure measurements using the proposed device, spring rates should be in the region of 0.5 to 2 N/mm.

Figure 17:
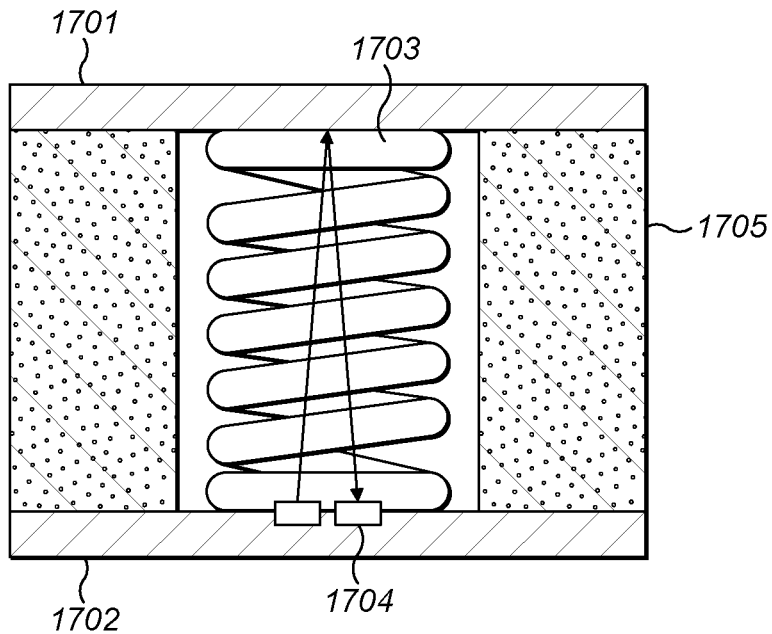
FIG. 17 illustrates a schematic cross-sectional view of a sensor embodying the present invention.

For shrouding the spring from external view, there can be several options. FIG. 17 illustrates an embodiment in which a spring is arranged inside a foam or similar material. The foam may be a cylindrical shape with the spring arranged in the central region or the foam may be two separate items flanking a central spring.

FIG. 17 illustrates an example in which a reflector 1701 and flexor substrates 1702 are arranged either side of the spring 1703. An optical device 1703 is arranged on the flexible substrate which emits light and senses light reflected off the reflector 1704. As the spring 1703 compresses the light detected by the optical device 1704 will be varied. The foam 1705 functions to protect the spring and shroud it from external view. Optionally, the foam 1705 will have a very low compression such that it has a negligible effect on the operation of the spring. Foams with higher compression may require additional force on the bandaging to compress down and therefore complicate the measurements. Also the hysteresis from the foam can be higher relative to the spring which must be factored into calculations.

Figure 18:
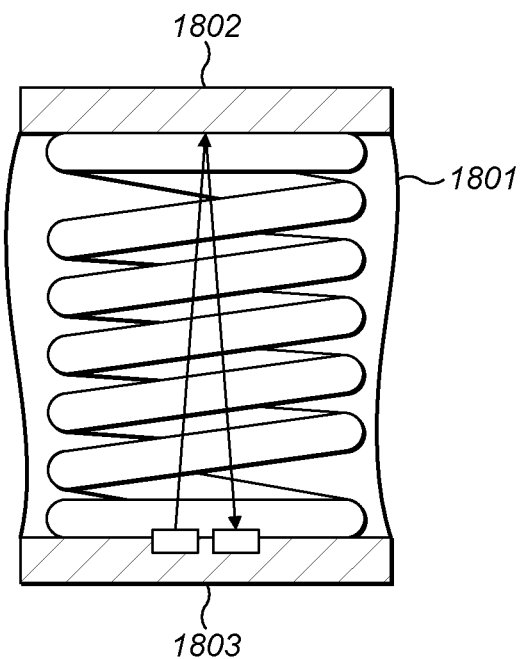
FIG. 18 is a schematic cross-sectional view of an alternative sensor of embodying the present invention.

A preferred solution to shroud the spring from external view is a flexible, thin membrane or a cloth as illustrated in FIG. 18, having no compression effect. The flexible membrane 1801 is affixed to the edge of the reflector 1802 or substrate 1803 or both. The membrane or cloth 1801 may be glued.

Figure 19:
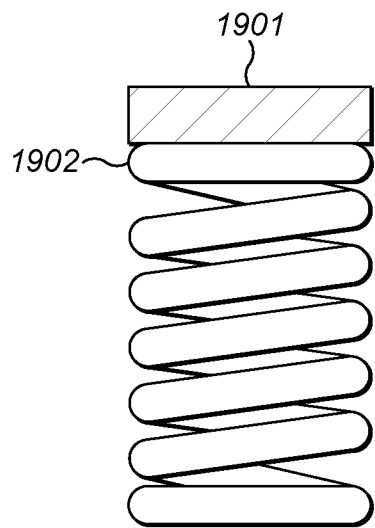
FIG. 19 illustrates a spring and reflector configuration.
Figure 20:
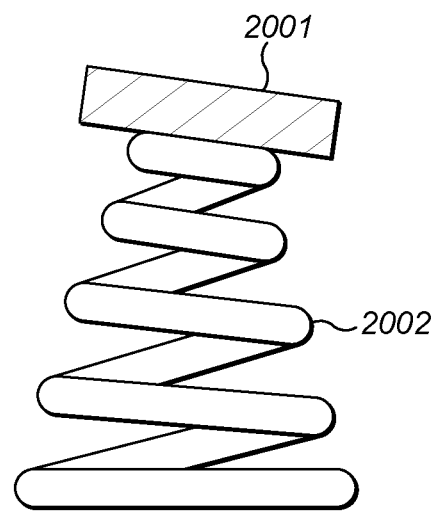
FIG. 20 illustrates an alternative spring and reflector configuration.

In general cylindrical springs may be preferred because the reflector can be placed in such a way that there is no possibility of tilting during the bandaging. Tilting may cause a change in optical path length and consequently an inaccurate reading. Such tilting is illustrated in FIGS. 19 and 20, with FIG. 19 illustrating untilted reflector 1901 on a cylindrical spring 1902. FIG. 20 illustrates a tilted reflector 2001 on a conical spring 2002.

Figure 21:
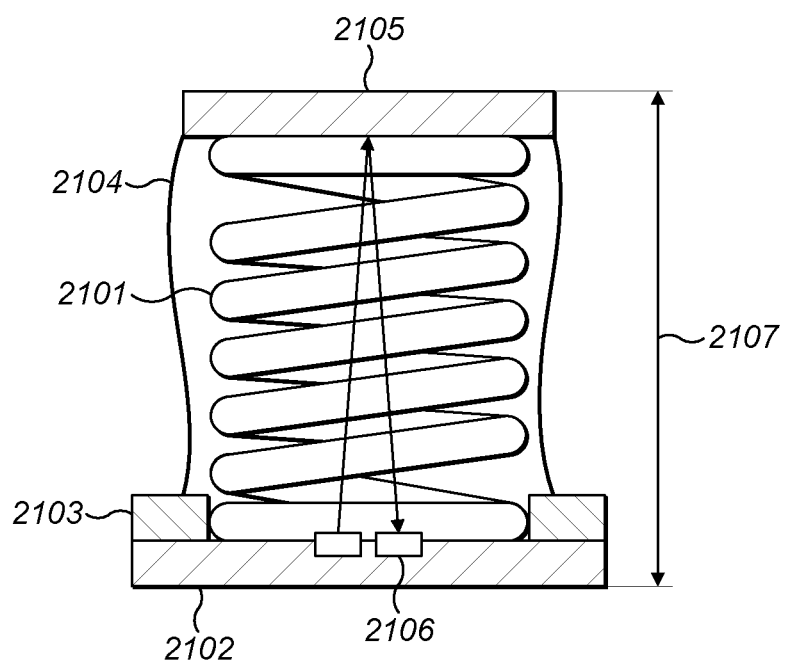
FIG. 21 is a schematic cross-sectional view of an exemplary sensor embodying the present invention.

FIG. 21 illustrates an overall schematic architecture of the sensor device utilising a cylindrical spring 2101. On a flexible interconnect strip 2102 is arranged a structured rigid mount 2103 which houses the optical devices 2106 and the microspring 2101. A white, plastic, disc-type reflector 2105, having a diameter similar to the outer diameter of the spring 2101 (in the region of 10 mm) is glued onto the spring. White, disc type is preferable. The glue is applied in such a way that it is only around the edges of the disc, keeping the central region well clear so as do not cause any interruption to the light received from the LED of the optical devices 2106. The flexible membrane 2104 is glued to the outer edge of the reflector and the support structure 2103.

The overall height of the sensor structure 2107 should ideally be in the range of 3 mm. Accordingly, with such a sensor architecture, when pressure is applied to the reflector, the distance between the reflector and the optical devices is varied and the light reflected by the reflector back to the optical device varies in accordance with the distance change. Thus, the pressure applied to the reflector can be determined by detecting the light received at the optical devices and performing subsequent measurements and calibration. As indicted above, the configuration and calibration indicated throughout the present description would be applied to the example in which the compressible spacer is a spring or comprises a spring.

An experiment for demonstrating the principles of the invention will now be described.

For leg ulcer management, graduated compression bandaging is used where an elasticated bandage is wrapped around the ulcerated leg. The pressure (applied by the bandage) is high at the ankle (typically 30 to 40 mmHg) and gradually decreasing just below the knee (typically 10 to 15 mm Hg). The main application of the present invention concerns recording the under-bandage graduated pressure along the length of the ulcerated leg. Five pressure sensing points are provided by this exemplary sensor strip.

Sensors, as shown and described in FIGS. 11 and 21, have been fabricated and tested for the above application. Flexible polymer strips; 50 micron thick, 300 mm long and 12 mm wide with metal traces (interconnect) have been used as substrates to construct sensor strips. Each sensor strip having 5 sensors spaced 6 cms apart. The spacings are appropriate for under-bandage pressure measurements.

The experimental sensors comprise base plates, optical devices (light emitting diode and a phototransistor combination GP2S60 from Sharp™), micro springs made of stainless steel and white plastic reflectors placed on top of the micro springs.

An open-source programmable electronic platform Arduino™ was used to trigger the light emitting diodes and receive signals from the phototransistor via the reflector. Codes were written in the Arduino programming language using the Arduino development environment to produce Force vs Voltage graphs.

Figure 22:
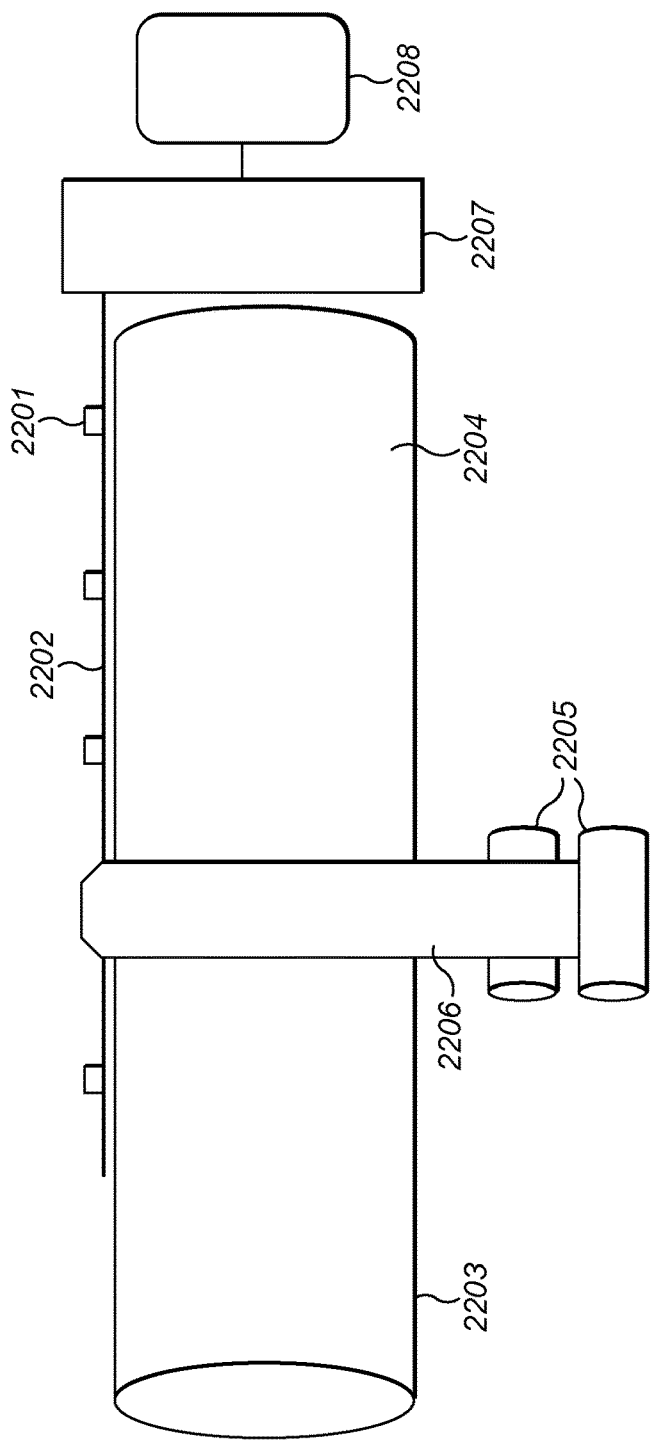
FIG. 22 illustrates an experiment for evaluating an exemplary sensor.

The experimental setup is shown in FIG. 22.

A 24 cm circumference hollow plastic tube 2203 (mimicking a human leg) was used for mounting the sensor strip 2202. Commercially available elasticated bandage 2206, routinely used for compression bandaging (from KTwo) was used to provide the desired pressure on sensors 2201. Also a commercially available Velband dressing 2204 (again routinely used in the procedure) was wrapped on the tube first, before placing the sensor strip 2202.

For this experiment the bandage 2206 was wrapped on each of the sensor 2201 individually. And at both ends of the bandage 2206 equal weights 2205 (50 gm on either side, total 100 gm) were used to apply force on the sensor reflector plate. Application of the weights caused the reflector height to reduce, relative to the phototransistor surface. The output current from the phototransistor increased, which was recorded in the electronic control unit 2207 as a voltage, for the applied weight. In this manner, the weights were increased progressively from 100 gm to 1000 gm in step of 100 gm and force vs voltage curve was produced for each sensor. Pressure was then calculated using area of the base plate. All the five sensors were characterised and five sets of pressure vs voltage curves were produced. All the curves were then displayed on the monitor 2208 as bar graphs.

Result: all the sensors responded as predicted, under load, reproducibly. Since the optics used were non-linear and also the stainless steel micro springs used have nonlinear response, the resulting pressure vs voltage curves were also nonlinear, which is not a problem. The high accuracy optical devices combined with low hysteresis stainless steel micro springs provided an ideal combination to produce a robust and accurate under-bandage pressure measurement technology. With the experimental setup described above, pressures ranging from 10 mmHg to 100 mmHg was easily and reproducibly reached. This range is typically adequate for under-bandage pressures to be applied in real procedures. Furthermore, using the developed software it has also been possible to set the desired limits of the pressure to be applied to patients e.g. 40 mmHg at the ankle to 10 mmHg just below the knee. The need for having controllable limits is dictated by the fact that not all patients can tolerate the high pressures prescribed by clinicians.

Other than pneumatic based single point sensors, which are not considered to be reliable, hitherto there are no reports of accurate under-bandage pressure measurement technology involving multiple sensing elements, appropriate for leg ulcer management.

Figure 23:
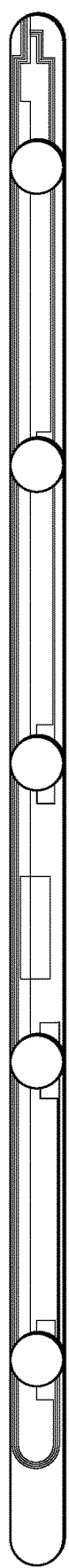
FIG. 23 illustrates an exemplary sensor strip.

FIG. 23 illustrates an exemplary sensor strip.

The invention claimed is:

1. A sensor suitable for measuring the pressure applied by a bandage, the sensor comprising an elongate strip having a sensor region, the sensor region comprising:
   a base plate;
   a top plate;
   a compressible spacer positioned between the base plate and the top plate; and,
   an electronic sensing apparatus configured to detect distance between the top plate and the base plate,
   wherein the top plate is arranged to compress the compressible spacer and arranged such that the bandage exerts a force on the surface of the top plate perpendicular to the surface when the sensor is positioned between the bandage and a limb,
   wherein the width of the top plate is calculated according to the equation:

$$R = (H/2) + (W^2/8 \times H)$$

where R is the radius of the limb around which the bandage is to be wrapped, H is a gap between the bandage and the centre of the surface of the top plate when wrapped around the limb and W is the width of the top plate.

2. The sensor according to claim 1, in which the width of the top plate is less than 15 mm.

3. The sensor according to claim 1, in which the electronic sensing apparatus comprises a light source and an optical sensor arranged to detect light emitted from the light source.

4. The sensor according to claim 1, in which the electronic sensing apparatus comprises a capacitor, wherein each conductive plate of the capacitor is coupled to the top plate and base plate respectively.

5. The sensor according to claim 4, in which the compressible spacer is configured between the conductive plates of the capacitor as a dielectric.

6. The sensor according to claim 1, in which the compressible spacer has a Young's modulus of approximately 0.4 GPa, a tensile strength in a first direction of approximately 0.3 N/mm$^2$, a tensile strength in a second direction of approximately 0.15 N/mm$^2$ and a density of approximately 20 Kg/m$^3$.

7. The sensor according to claim 1, in which the compressible spacer is made from foam.

8. The sensor according to claim 1, in which the compressible spacer comprises a microspring.

9. The sensor according to claim 8, in which the microspring is arranged to reduce tilting.

10. The sensor according to claim 8, in which the microspring is cylindrical or conical.

11. The sensor according to claim 8, in which the microspring is wave-type.

12. The sensor according to claim 8, in which the microspring is affixed to the base plate and the top plate so as to leave a central region of the spring free of adhesive.

13. The sensor according to claim 1, in which the compressible spacer comprises a membrane or cloth attached to an edge of the top plate.

14. The sensor according to claim 1, in which the compressible spacer has a thickness of less than 3 mm.

15. The sensor according to claim 1, in which the sensor is coated with a low friction material to facilitate removal of the sensor from under the bandage.

16. The sensor according to claim 1, further comprising a structured pedestal configured on the surface of the top plate.

17. The sensor according to claim 1, the sensor further comprising a control unit, wherein the control unit is configured to:

receive data from the electronic sensing apparatus indicative of the distance between the top plate and the base plate; and, output an indication of the pressure exerted on the sensor by the bandage when wrapped around the sensor based on the received data.

18. The sensor according to claim 1, in which the sensor comprises a plurality of sensor regions arranged along the length of the elongate strip.

19. The sensor according to claim 18, in which the sensor regions are spaced apart by a flexible connector.

20. The sensor according to claim 19, in which the flexible connector comprises a polymer elongate strip having a thickness between 50 microns and 1 millimetre.

21. A method for testing the compression of a bandage around a limb, which comprises winding the bandage around the limb and a sensor according to claim 18, the sensor being positioned along the limb and the length of the intended bandage, and determining the pressure applied to the limb at a plurality of points corresponding to the sensor regions.

* * * * *